(12) United States Patent
Ravi et al.

(10) Patent No.: US 10,874,879 B2
(45) Date of Patent: Dec. 29, 2020

(54) SYSTEM AND METHOD FOR ENDO-RECTAL RETRACTION AND ORGAN IMMOBILIZATION FOR RADIOTHERAPY OF THE PELVIS

(71) Applicant: Sunnybrook Research Institute, Toronto (CA)

(72) Inventors: Ananth Ravi, Toronto (CA); Harry Easton, Unionville (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 628 days.

(21) Appl. No.: 15/517,776

(22) PCT Filed: Oct. 8, 2015

(86) PCT No.: PCT/CA2015/051018
§ 371 (c)(1),
(2) Date: Apr. 7, 2017

(87) PCT Pub. No.: WO2016/054740
PCT Pub. Date: Apr. 14, 2016

(65) Prior Publication Data
US 2017/0312546 A1    Nov. 2, 2017

Related U.S. Application Data

(60) Provisional application No. 62/061,399, filed on Oct. 8, 2014.

(51) Int. Cl.
*A61N 5/10* (2006.01)
*G01T 1/10* (2006.01)

(52) U.S. Cl.
CPC ......... *A61N 5/1071* (2013.01); *A61N 5/1075* (2013.01); *G01T 1/10* (2013.01);
(Continued)

(58) Field of Classification Search
CPC ............... A61N 5/1071; A61N 5/1075; A61N 2005/1094; A61N 2005/1087; A61N 2005/1097; G01T 1/10
(Continued)

(56) References Cited

U.S. PATENT DOCUMENTS 5,624,537 A * 4/1997 Turner ............ C12Q 1/002
204/402
7,831,016 B2 * 11/2010 Saoudi ............ A61N 5/1048
378/65

(Continued)

FOREIGN PATENT DOCUMENTS

| EP | 2606825 A1 | 6/2013 |
|---|---|---|
| WO | 2003062855 A1 | 7/2003 |
| WO | 2010080905 A2 | 7/2010 |

OTHER PUBLICATIONS

Bard Medical. Colon/Rectal Tubes webpage. Accessed online at http://www.bardmedical.com/products/bowel-gastric-management/bowel-management/colonrectal-tubes/ on Oct. 31, 2016.
(Continued)

*Primary Examiner* — David P Porta
*Assistant Examiner* — Meenakshi S Sahu
(74) *Attorney, Agent, or Firm* — Quarles & Brady LLP

(57) ABSTRACT

A system for monitoring doses from an ionizing radiation source to a treatment region of a patient and immobilizing a body cavity relative to the treatment region, is provided. The system includes a probe body for insertion into the body cavity. The probe body separates the body cavity from the treatment region to reduce exposure to doses from the ionizing radiation source. Radiation detectors are disposed along the probe body to measure at least one dose. A slot disposed adjacent the radiation detectors receives a dosimetry film that, upon exposure to the one or more doses from the ionizing radiation source, indicates a quantification of
(Continued)

the doses. A coupling is in fluid communication with a removable sheath having coupled thereto a vacuum or a pump to remove fluid or gas from the body cavity and ensure inner wall of the body cavity is in contact with the sheath.

24 Claims, 6 Drawing Sheets

(52) U.S. Cl.
CPC ............... *A61N 2005/1087* (2013.01); *A61N 2005/1094* (2013.01); *A61N 2005/1097* (2013.01)

(58) Field of Classification Search
USPC ..................................................... 250/484.5
See application file for complete search history.

(56) References Cited

U.S. PATENT DOCUMENTS

| | | | |
|---|---|---|---|
| 2009/0250618 A1 | 10/2009 | Simon | |
| 2012/0165652 A1* | 6/2012 | Dempsey | A61B 90/37 600/411 |
| 2012/0230574 A1* | 9/2012 | Rozenfeld | A61B 6/032 382/131 |
| 2014/0257013 A1 | 9/2014 | D'Andrea | |

OTHER PUBLICATIONS

Bayer HealthCare. PRO-TEKT Endorectal Balloon webpage. Accessed online at http://www.medrad.com/en-us/info/products/Pages/ProstateImmobilizer.aspx on Mar. 13, 2014.

BK Medical. Endocavity Biplane Transducer booklet. May 2016 edition. Accessed online at http://www.bkmed.com/8848_en.htm.

Court, L. Motion and shape change when using an endorectal balloon during prostate radiation therapy. Radiother & Oncol. 2006;81(2):184-9.

Elsayed H, et al. Organ movements and dose exposures in teletherapy of prostate cancer using a rectal balloon. Strahlenther Onkol. 2007;183:617-24.

European Patent Office. Extended European Search Report for application 15848657.1, dated Oct. 4, 2018, 10 pages.

Ghilezan M. Prostate gland motion assessed with cine-magnetic resonance imaging. Int J Radiat Oncol Biol Phys. 2005;62(2):406-17.

Gladwish A, et al. Prostatic displacement during extreme hypofractionated radiotherapy using volumetric modulated arc therapy (VMAT). Radiat Oncol. 2014;9:262.

Hung AY, et al. Minimal benefit of an endorectal balloon for prostate immobilization as verified by daily localization. Med Dosim. 2011;36(2):195-9.

International Searching Authority, International Search Report and Written Opinion, PCT/CA2015/051018. dated Jan. 12, 2016, 10 pages.

Isacsson, U. et al., A Method to Separate the Rectum from the Prostate During Proton Beam Radiotherapy of Prostate Cancer Patients, Acta Oncologica, 2010, 49: 500-505.

Jones BL, et al. Dosimetric and deformation effects of image-guided interventions during stereotactic body radiation therapy of the prostate using an endorectal balloon. Med Phys. 2012;39(6):3080-3088.

Kim DWN, et al. Predictors of rectal tolerance observed in a dose-escalated phase 1-2 trial of stereotactic body radiation therapy for prostate cancer. Int J Radiat Oncol Biol Phys. 2014;89(3):509-17.

Nicolae et al., Clinical Evaluation of an Endorectal Immobilization System for Use in Prostate Hypofractionated Stereotatic Ablative Body Radiotherapy (SABR), Radiation Oncology, 2015, 10: 122, 8 pages.

Nilsson, K. et al., Decreasing the Dose to the Rectal Wall by Using a Rectal Retractor During Radiotherapy of Prostate Cancer: A Comparative Treatment Planning Study, Journal of Radiotherapy, vol. 2014, Hindawi Publishing Corporation, 7 pages.

Padhani A, et al. Evaluating the effect of rectal distension and rectal movement on prostate gland position using cine MRI. Int. J. Radiat. Oncol. Biol. Phys. 1999;44(3):525-533.

SMD Medical. Rectal Tube Webpage. Accessed online at http://www.smd-medical.com/upfile/Proimage/rectal%20tube.pdf on Apr. 29, 2016.

Smeenk RJ, et al. An endorectal balloon reduces intrafraction prostate motion during radiotherapy. Int J Radiat Oncol Biol Phys. 2012;83(2):661-669.

Wang CW, et al. Set-up errors due to endorectal balloon positioning in intensity modulated radiation therapy for prostate cancer. Radiother. Oncol. J. 2007;84(2):177-184.

* cited by examiner

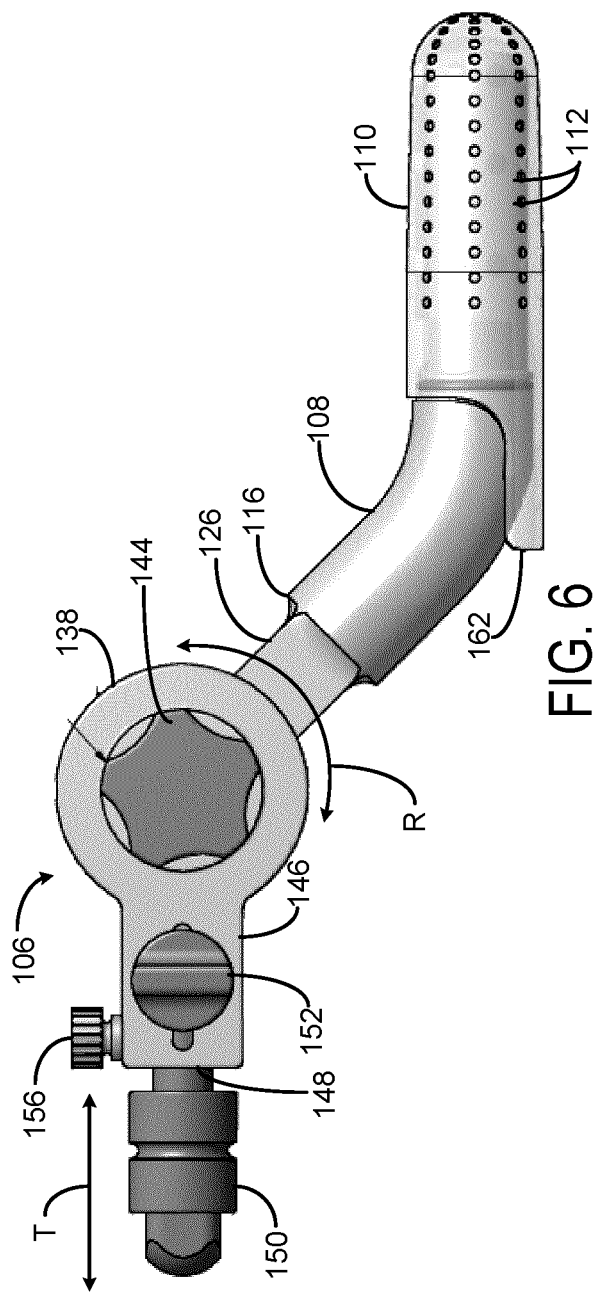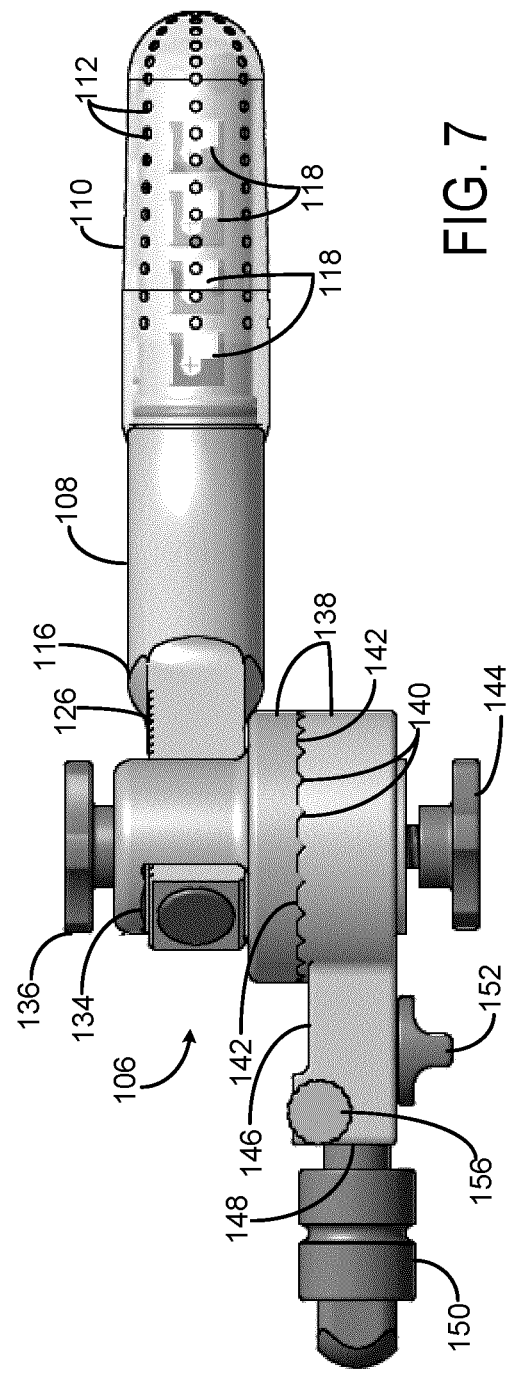

SYSTEM AND METHOD FOR ENDO-RECTAL RETRACTION AND ORGAN IMMOBILIZATION FOR RADIOTHERAPY OF THE PELVIS

CROSS-REFERENCE TO RELATED APPLICATIONS

This application represents the national stage entry of PCT International Application PCT/CA2015/051018 filed Oct. 8, 2015, which claims the benefit of U.S. Provisional Application 62/061,399 filed Oct. 8, 2014. The contents of this application are hereby incorporated by reference as if set forth in their entirety herein.

BACKGROUND OF THE INVENTION

The field of the invention is systems and methods for endorectal retraction during radiotherapy for prostate cancer. More particularly, the invention relates to systems and methods for non-invasively immobilizing the prostate gland during each treatment fraction while providing reproducible rectal retraction during subsequent treatments, thereby reducing the volume of normal tissue receiving high doses when treating prostate cancer while ensuring accurate coverage of the prostate gland.

In ablative radiotherapy of prostate cancer the dose that can be safely delivered to the prostate is limited by adjacent organs at risk (OARs), primarily the rectum and the bladder. Attempts to reduce the dose to the rectum involve advanced image guidance techniques that are used to ensure accurate patient positioning in concert with the latest in dose delivery technology to produce dose distributions with steep gradients and organs at risk sparing. However, to achieve the dose required to ablate prostate cancer, additional intervention is required to ensure the prostate is stationary during treatment and the adjacent organs at risk are spared.

Evidence suggests that prostate cancer cells are sensitive to large doses per fraction (hypofractionation). This has driven a trend towards the adoption of Stereotactic Ablative Body Radiotherapy (SABR), for localized prostate cancer. The adoption of SABR has the additional benefit of improving patient access to hypofractionated treatments while simultaneously improving the cost-effectiveness of prostate radiotherapy. SABR techniques rely on an external source of radiation to deliver the radiation dose to the prostate; as such, SABR treatment planning must account for any potential prostate motion. This is typically achieved through the addition of a planning target volume (PTV) margin around the prostate. However, unacceptable late urinary and rectal complications can develop if the safety margins are too large to account for positional uncertainties, especially with such large fractional doses.

One method to safely reduce margins is through the application of prostate immobilization strategies. One such strategy addresses rectal motion and filling, which has consistently been a significant predicator of prostate motion. This strategy involves the use of endorectal balloons (ERB) to control the volume of the rectum and therefore indirectly immobilize the prostate. Conventionally, the ERB is placed in the rectum and inflated with air to expand the rectum. The anterior rectal wall moves toward the prostate and displaces it frontally, while the posterior wall remains in its position resulting in an increased distance between the prostate and the posterior wall. Since the endorectal balloon reduces variations in rectum filling and immobilizes the prostate, the PTV margin can be reduced, which results in a lower dose to the posterior rectal wall.

While endorectal balloons have been effective, the mechanism of inflating the ERB raises the anterior surface of the rectum into the high dose region of the treatment plan. This associated deformation of local anatomy makes it difficult to achieve dosimetric constraints that are on par with other ablative radiotherapy modalities, such as brachytherapy. While controversy remains in regards to the protective nature of the displaced normal rectal tissue, it is generally agreed that lower rectal doses results in lower rates of rectal toxicity.

An alternative to endorectal balloons has been the use of injectable/implantable spacers or polymeric gels. The spacer gel is injected between the prostate gland and the anterior rectal wall, which increases the distance between, resulting in significantly decreased dose to the rectal wall. Although the rectal doses using this system are lower due to the physical separation of the prostate from the rectum, no evidence is available that any substantial prostate immobilizing effect is produced. These methods are also quite invasive requiring a transperineal incision or interstitial needle placement.

It would therefore be desirable to provide a system and method for an endorectal retraction system aimed at consistently immobilizing the prostate gland during each treatment fraction, while achieving separation of the rectum from the prostate using relatively non-invasive methods, thereby increasing the space between anterior rectal wall and posterior prostate. It would also be desirable to provide favorable anterior rectal wall dosimetry with minimal organ deformation.

SUMMARY OF THE INVENTION

The present invention overcomes the aforementioned drawbacks by providing a system and method for separating a body cavity, such as the anterior rectal membrane, away from a treatment region, such as the posterior prostate surface, using a retractor system. The retractor system creates sufficient separation between the sensitive organ at risk and the diseased prostate. Further, the position of the retractor can be characterized and quantified to ensure reproducible setup so that the treatment plan is reproduced during delivery. The retractor also acts as an immobilization device ensuring that the rectum does not rise and move into the high dose region. In addition, the retractor limits prostatic motion. The rectal retractor further includes a plurality of radiation detectors such that the dose can be measured and monitored after treatment delivery to ensure that treatment has been accurately delivered.

It is an aspect of the invention to provide a system for monitoring doses from an ionizing radiation source to a treatment region of a patient. The system includes a probe body for insertion into a body cavity near the treatment region of the patient. A plurality of radiation detectors are disposed along a proximal end of the probe body to measure at least one dose from the ionizing radiation source. A slot is disposed adjacent the plurality of radiation detectors. The slot is configured to receive a dosimetry film that, upon exposure to the at least one dose from the ionizing radiation source, indicates a quantification of the at least one dose from the ionizing radiation source. In addition, the probe body is dimensioned to separate a portion of the body cavity from the treatment region to reduce exposure of membranous tissue surrounding the body cavity to the at least one dose from the ionizing radiation source.

It is another aspect of the invention to provide a device for immobilizing a body cavity relative to an anatomic region-of-interest. The device includes a probe for insertion into the body cavity. A removable sheath, including a plurality of perforations, is configured to receive the probe. A coupling in fluid communication with the removable sheath is configured to be coupled to at least one of a vacuum and a pump to actively remove at least one of fluid and gas from the body cavity.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6 a side view of the probe body of FIG. 3 coupled to a probe adjustment member and a removable sheath;

FIG. 7 is a top view of the probe body coupled to the probe adjustment member and the removable sheath of FIG. 6;

DETAILED DESCRIPTION OF THE INVENTION

A retractor system for use in prostate, bladder, and gynecological radiotherapy, as well as prostate, bladder, and gynecological brachytherapy, for example, is provided. In some embodiments, the retractor system can be used in the treatment of gynecological disorders of the cervix, uterus, and vagina. The retractor system may be configured to immobilize a body cavity relative to an anatomic region-of-interest. In one example, the retractor system inhibits prostate intrafraction and interfraction motion over the course of radiation treatment by insertion of a probe body into the body cavity. The effect of the retractor system on both prostate coverage and dose received by organs-at-risk (OAR), in particular the anterior rectal wall, can be evaluated using a plurality of radiation detectors disposed along the probe body. Additionally, or alternatively, in-vivo dose verification and quality assurance (QA) using dosimetry film received by a slot provided in the probe body is contemplated.

Figure 1:
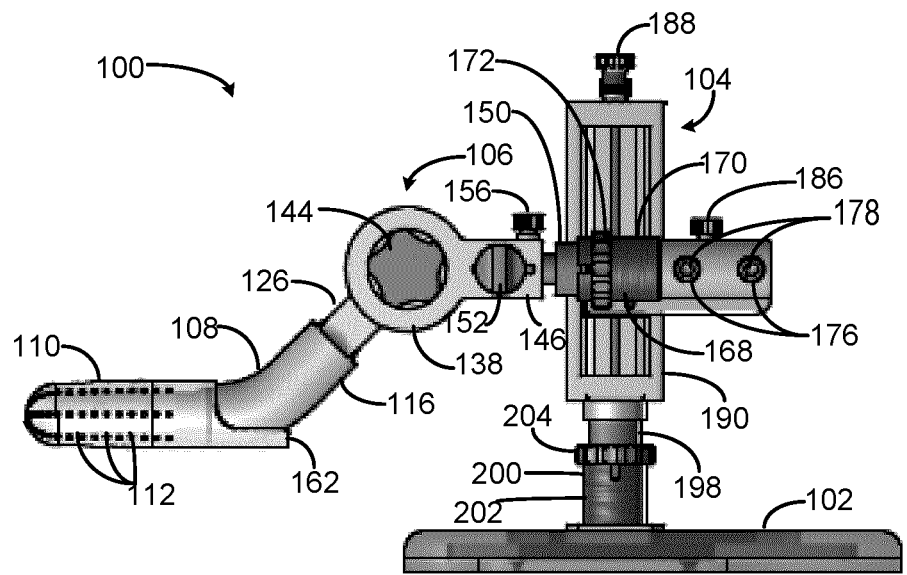
FIG. 1 is a side view of an exemplary rectal retractor system according to the present invention.
Figure 2:
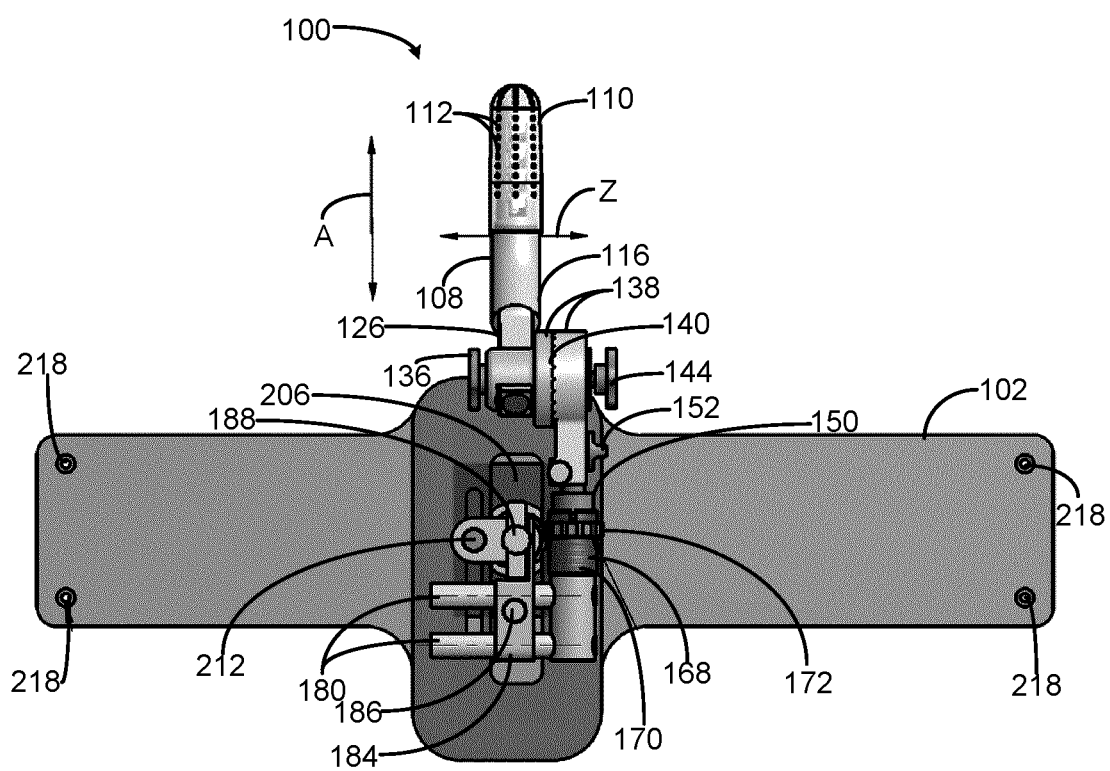
FIG. 2 is a top view of the exemplary rectal retractor system of FIG. 1.

Referring particularly now to FIGS. 1 and 2, the retractor system 100 generally includes a base 102, a stage 104 vertically extending from the base 102, and a probe adjustment member 106 coupled to the stage 104 and configured to engage a probe body 108. The probe body 108 may be inserted into a body cavity (not shown), such as the rectum, of a patient to retract the body cavity away from a treatment region, such as the prostate gland, during a radiotherapy procedure. In some embodiments, a removable sheath 110 having a plurality of perforations 112 may be inserted over the probe body 108 to permit gas, which may include rectal gas, to pass out of the body cavity, which may be the rectum. In addition, negative pressure can be applied through the addition of an external vacuum pump to ensure complete contact of the rectal membrane with the probe body 108 to maintain retraction of the anterior surface throughout treatment.

In one non-limiting example, the retractor system 100 may be a rectal retractor system for separating the anterior rectal membrane away from the posterior prostate surface to create sufficient separation between the rectum, which is a sensitive OAR, and the prostate. This separation can allow for a spatial dose gradient such that the high ablative doses given during the radiotherapy procedure can drop off to doses that are safe for the rectum. Due to the various adjustment mechanisms provided on the retractor system 100, as will be described in further detail below, the position of the retractor system 100 can be characterized and quantified to ensure reproducible setup so that the treatment plan is reproduced during delivery. The retractor system 100, in some embodiments, may act as an immobilization device to ensure that the body cavity (e.g., the rectum) does not rise and move into the high dose region. Additionally, or alternatively, the retractor system 100 can monitor doses from an ionizing radiation source to a region-of-interest (e.g., the prostate gland). Furthermore, the retractor system may be indexed and fixed to the treatment bed, thereby providing immobilization for both the rectum and the prostate.

Figure 3:
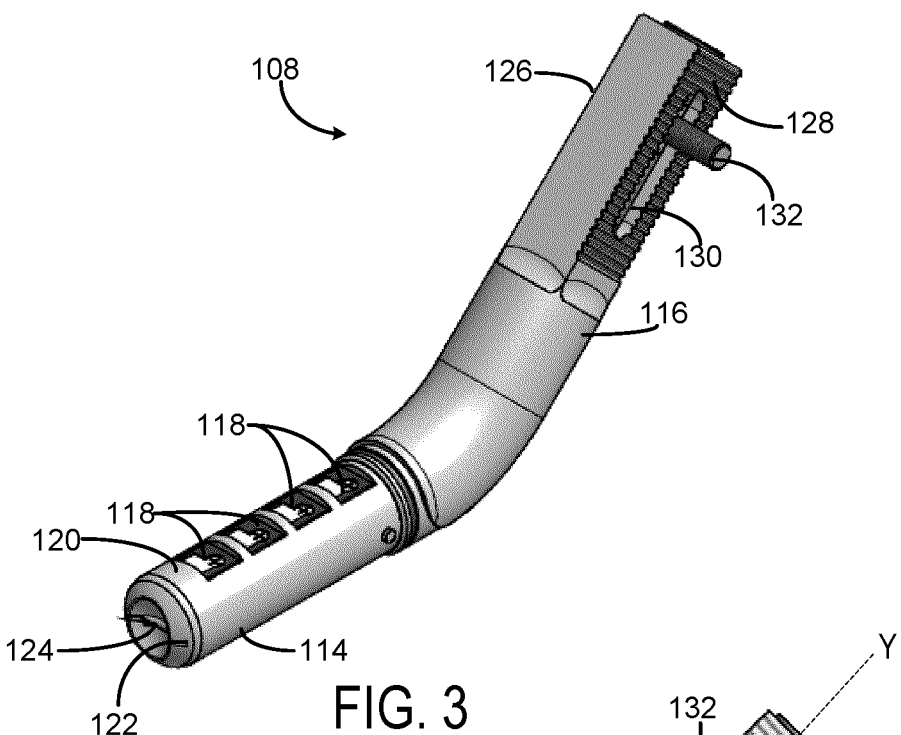
FIG. 3 is a perspective view of a probe body to be implemented into the rectal retractor system including a plurality of optical luminescence dosimeters and film dosimeters for measuring doses when practicing embodiments of the present invention.
Figure 4:
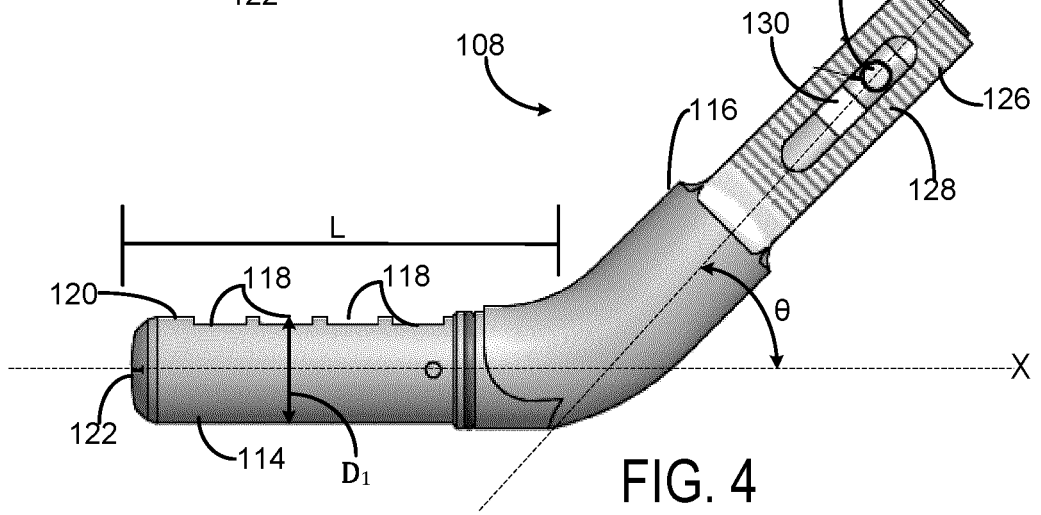
FIG. 4 is a side view of the probe body of FIG. 3.
Figure 5:
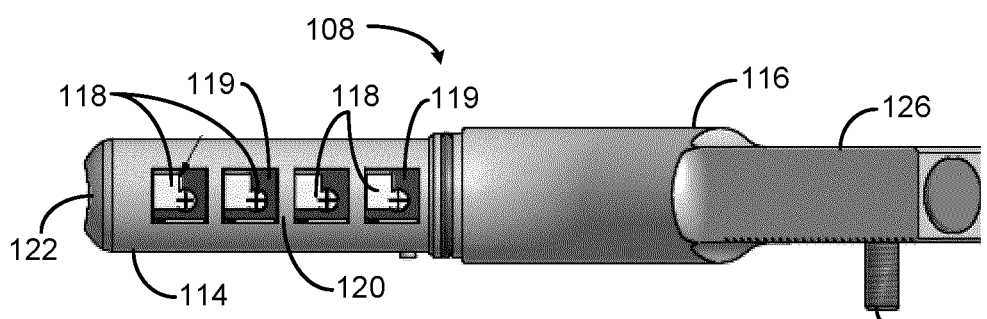
FIG. 5 is a top view of the probe body of FIG. 3.

Turning now to FIGS. 3-5, the probe body 108 having an elongate, cylindrical shape is shown. In other embodiments, the shape of the probe body 108 can be of other configurations, such as a hemispherical cylinder. However, the probe body 108 may be any suitable shape to provide immobilization. The probe body 108 may be constructed out of materials that can be steam sterilized, for example, and used repeatedly for subsequent radiotherapy treatments. The probe body 108 may include a proximal end 114 integrally coupled to a distal end 116. The proximal end 114 may have a diameter $D_1$ between about 10 millimeters and about 25 millimeters, however the diameter $D_1$ may have any dimension so long as the probe body 108 can sufficiently be received by the body cavity. Similarly, the proximal end 114 may include a length dimension L that extends along a first axis X, as shown in FIG. 4. The length dimension L of the proximal end 114 may be between about 70 millimeters and about 140 millimeters, however the length L may have any dimension so long as the probe body 108 can be sufficiently received by the body cavity.

With continued reference to FIG. 4, the proximal end 114 of the probe body 108 may extend along the first axis X, and the distal end 116 of the probe body 108 may extend along a second axis Y, thereby creating an angle θ. The angle θ may be between about 35 degrees and about 45 degrees, such that when the probe body 108 is inserted into a body cavity, such as the rectum, of the patient, the body cavity is separated from the treatment region.

In addition, the probe body 108 includes a plurality of radiation detectors 118 disposed along the proximal end 114 of the probe body 108. In one embodiment, the plurality of radiation detectors 118 may be disposed along a top surface 120 of the probe body 108, such that the plurality of radiation detectors 118 are adjacent an inner wall (e.g., the anterior rectal membrane wall) of the body cavity during a radiotherapy treatment. A gasket 119, constructed of rubber for example, may also be provided on the proximal end 114 of the probe body 108 to form a seal for the radiation detectors 118, as shown in FIG. 5. The seal formed by the gasket 119 can inhibit bodily fluids from contaminating the radiation detectors 118.

The plurality of radiation detectors 118 may be configured to measure one or more doses from an ionizing radiation source along the surface of the body cavity. In one non-limiting example, the plurality of radiation detectors 118 may be optically stimulated luminescence (OSL) detectors for measuring the ionizing radiation. Based on an output from the plurality of radiation detectors 118, the quality of the delivered radiotherapy treatment can be assessed and any deviations from the intended plan can be identified. Thus, the output provided by the plurality of radiation detectors 118 can be used to monitor subsequent doses after treatment delivery to ensure that treatment has been accurately delivered.

As shown in FIG. 3, the probe body 108 may further include a slot 122 at the proximal end 114 of the probe body 108. The slot 122 may be disposed adjacent the plurality of radiation detectors 118 and dimensioned to receive a dosimetry film 124. Upon exposure to one or more doses of ionizing radiation, the dosimetry film 124 can indicate a quantification of the one or more doses. Thus, the dosimetry film 124 can measure in-vivo absolute dose monitoring. In one non-limiting example, the dosimetry film 124 may be a radiographic or radiochromic film. For example, the radiochromic film can be a GafChromic film, such as GafChromic EBT3 film. In the example of GafChromic EBT3 film, the film strips may be evaluated using FilmQA software provided by Ashland Company of Covington, Ky. to evaluate the color changes of the GafChromic EBT3 film.

In an alternative embodiment, a software program may be used to compare the dosimetry film 124 to the planned dose distribution. The software program may be configured to resample the dose distribution in the plane of the dosimetry film 124 and prepare the dosimetry film 124 for cross comparison with the measured film from the endorectal retractor system 100. Thus, the software program is responsible for resampling the treatment plan data, calculated dose distribution, and re-orienting the data in the plane of the measured dosimetry film 124 found in the probe body 108. By acquiring the calculated dose in the same plane as the dosimetry film 124, the end-user can compare the calculated/estimated dose with the measured film to provide end-to-end quality assurance. Without the resampling software program, comparison between the measured dosimetry film 124 and the calculated dose may not be easily achieved.

With continued reference to FIGS. 3-5, the distal end 116 of the probe body 108 may be a square, prism shaped member 126, for example, that is configured to be received by an opening of the probe adjustment member 106 (see FIG. 7). The square shaped member 126 may include a plurality of retention grooves 128 disposed along a surface of the square shaped member 126. A recess 130 may be provided on the surface of the square shaped member 126 within the plurality of retention grooves 128. The recess 130 may be dimensioned to receive a locking spindle 132 that extends outwardly therefrom and can translate along the second axis Y to adjust an overall height of the probe body 108 with respect to the body cavity of a patient. In an alternative embodiment, the locking spindle 132 for adjusting the probe body 108 height may be replaced by an adjustable cylindrical member (not shown) coupled to the stage 104 for adjusting the probe body 108 height.

As just described, the square shaped member 126 of the probe body 108 may be received by an opening 134 of the probe adjustment member 106, as shown in FIG. 7. A locking handle 136 may include internal threads (not shown) that engage external threads of the locking spindle 132, such that once the probe body 108 is adjusted to a desired height (i.e., by translating the locking spindle 132 within the recess 130), the locking handle 136 may be rotated to secure the probe body 108 in place. The probe adjustment member 106 may also allow for a rotational adjustment, as indicated by arrow R in FIG. 6.

In order to provide the rotational adjustment of the probe body 108, a pair of cylindrical members 138 may be rotated with respect to one another. Each of the cylindrical members 138 includes a plurality of gear-like teeth 140 disposed around a peripheral edge 142 that are configured to incrementally engage one another as one of the cylindrical members 138 is rotated. A rotational locking knob 144 may be rotated to lock the gear-like teeth 140 of the cylindrical members 138 together, thereby inhibiting undesired rotation of probe body 108. In some embodiments, in absence of the plurality of gear-like teeth 140, the distal end 116 of the probe body 108 may be coupled to a shaft (not shown) that is received by an opening in the cylindrical member 138 in order to lock the rotational motion of the probe body 108. In addition, one of the cylindrical members 138 may include numbered indicia (not shown) disposed along a surface thereof, for example, for accurate, rotational repositioning of the probe body 108 for subsequent treatments.

With continued reference to FIGS. 6 and 7, a support arm 146 may be integrally coupled to, and extend away from, for example, one of the cylindrical members 138. At an opposing end, the support arm 146 may include an aperture 148 dimensioned to receive a docking plunger 150. The docking plunger 150, as will be described in further detail below, may engage a docking socket of the stage 104. Additionally, the support arm 146 could be directly fixed to the vertical member of the translation stage 104. The docking plunger 150 is releasably connected to the support arm 146 and may be adjusted to increase or decrease a distance from the probe adjustment member 106 to the stage 104. More specifically, a translation knob 152 may be coupled to the docking plunger 150 and translated in a recess 154 disposed on the support arm 146 in the direction indicated by arrow T in FIG. 6. Upon a desired position of the docking plunger 150 in the aperture 148 of the support arm 146, a locking screw 156 may be tightened, by rotation for example, to lock the docking plunger 150 in place. Alternatively, the docking apparatus just described may be integrally formed with a docking socket 168 of the vertical stage 104.

As shown in FIGS. 6 and 7, the removable sheath 110 is configured to be received by the probe body 108. The removable sheath 110 includes a hollow cavity (see FIGS. 8 and 9) that is dimensioned substantially the same as the proximal end 114 of the probe body 108. Thus, the removable sheath 110 may allow active adherence of the inner wall of the body cavity to the probe body 108, thereby increasing immobilization of the body cavity. In some embodiments, the removable sheath 110 may be constructed from a polymeric material, such as polyether ether ketone (PEEK), that can be either sterilized for repeat or single use. Thus, the removable sheath 110 may be reusable or disposable. The plurality of perforations 112 may be circular in shape; however, the plurality of perforations 112 may be any suitable shape to permit liquid or gas (e.g., rectal gas), for example, to passively, or through the introduction of negative pressure, pass out of the body cavity (e.g., the rectum). In addition, the plurality of perforations 112 may exhibit any suitable perforation pattern depending on different configurations of the removable sheath 110.

Figure 9:
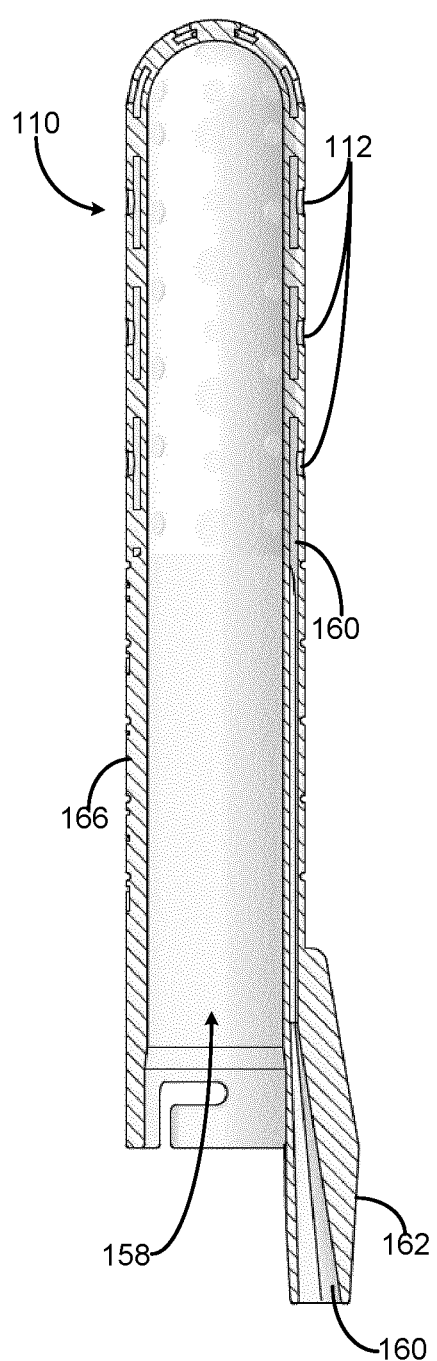
FIG. 9 is a side cross-sectional view of the exemplary removable sheath of FIG. 8 taken along line 9-9.

As shown in FIG. 9, each of the plurality of perforations 112 connect to a passageway 160 that allows gas to exit the body cavity. Additionally, or alternatively, a coupling 162 may be attached to the passageway 160. The coupling 162 may be in fluid communication with the passageway 160 of the removable sheath 110 and configured to connect to a vacuum or pump (not shown), for example. Thus, the vacuum or pump connected to the coupling 162 may provide an active suction process to remove liquid and/or gas from the body cavity, as well as ensure the body cavity (e.g., the rectal membrane) is adhered to the probe body 108 as the body cavity is separated from the anatomic region-of-interest (e.g., the prostate).

Figure 8:
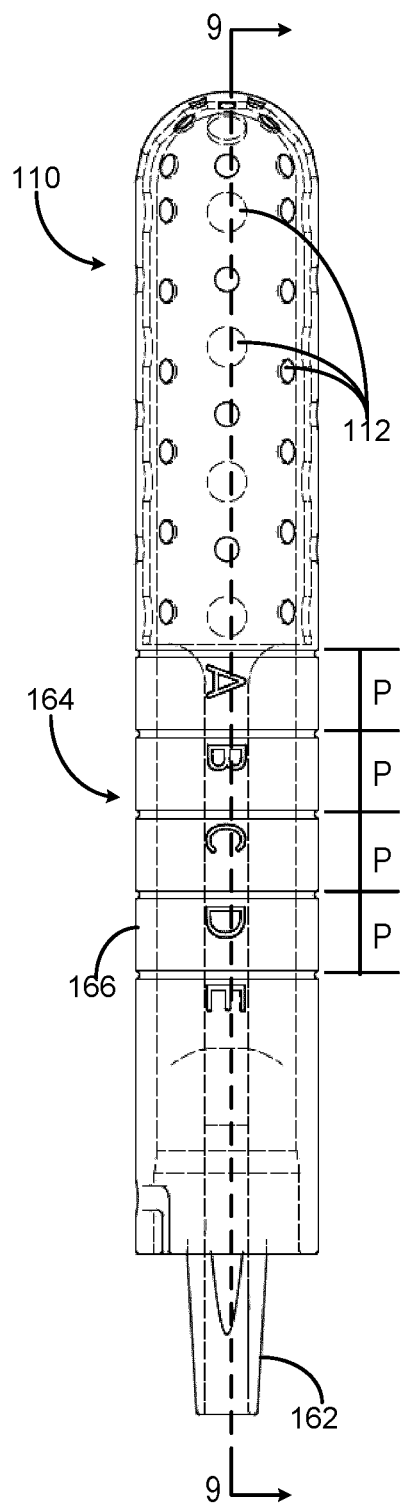
FIG. 8 is a top view of an exemplary removable sheath configured to engage the probe body according to one embodiment of the present invention.

By permitting liquid and/or gas to exit the body cavity, passively or actively, reproducibility of patient setup can be improved. In addition, measurement guides 164, as shown in FIG. 8, may also be provided to improve reproducibility of patient setup. In one non-limiting example, each measurement guide 164 may be circumferentially disposed, inscribed and/or embossed on an outer surface 166 of the removable sheath 110. Each measurement guide 164 may be spaced a predetermined distance P apart. The predetermined distance P may be between about 4 millimeters and about 12 millimeters, for example. Knowing the predetermined distance P may allow a user to know how far the probe body 108 is inserted into the body cavity. Thus, for radiotherapy treatments that require multiple doses, the patient setup of the probe body 108 can easily be reproduced for each dose.

Figure 10:
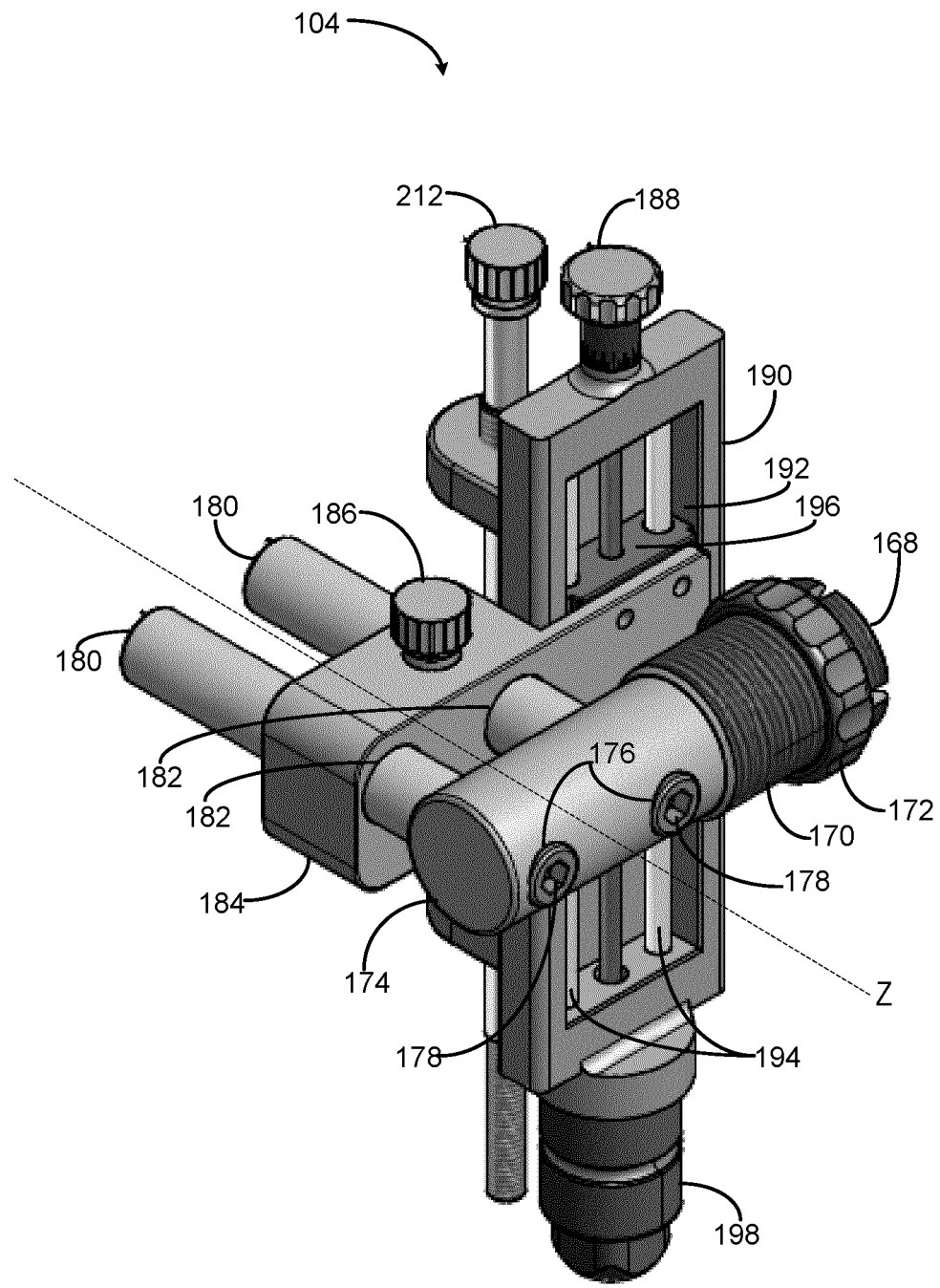
FIG. 10 is a perspective view of a vertical stage configured to receive the probe adjustment member and probe body of FIG. 6.

Turning now to FIG. 10, the stage 104, which is configured to connect to both the probe adjustment member 106 and the base 102, is shown. The stage 104 allows for height adjustment, lateral adjustment, and anterior-posterior adjustment of the probe body 108. Additionally, in some embodiments, the stage 104 may include the ability to adjust the angulation of the probe body 108. These adjustments may provide controlled motion to ensure that no dramatic changes in the probe body 108 position can occur, thereby potentially limiting the risk of injury to the patient.

The stage 104 includes the docking socket 168 configured to receive the docking plunger 150 of the probe adjustment member 106 (See FIGS. 1 and 2 for complete assembly). The docking socket 168 may include external threads 170 for engaging internal threads (not shown) of a safety ring 172. Thus, once the docking plunger 150 of the probe adjustment member 106 is seated in the docking socket 168, the safety ring 172 may be rotated about the external threads 170 to secure the connection between the docking plunger 150 and the docking socket 168. The docking socket 168 could also take the form of a thumb screw mechanism (not shown) that tightens onto the probe body 108 directly upon insertion into a slot of the stage 104.

With continued reference to FIG. 10, a cylindrical body 174 may be coupled to, or integrally formed with, the docking socket 168 of the stage 104. The cylindrical body 174 includes a pair of apertures 176 configured to receive a pair of fasteners 178, such as hex screws. Each fastener 178 may be coupled to a guide rod 180 that extends substantially perpendicular from the cylindrical body 174 along an axis Z. Although two guide rods 180 are depicted in FIG. 10, a single guide rod may be used, so long as rotational movement of the guide rod 180 about the axis Z is not permitted. Alternatively, more than two guide rods 180 may be used. In addition, the guide rod 180 may include numbered indicia (not shown) disposed along a surface of the guide rod 180, for example, for accurate repositioning of the probe body 108 for subsequent treatments.

The guide rods 180 can be received by a pair of apertures 182 extending through a support member 184 to allow lateral movement of the cylindrical body 174 and, subsequently lateral movement of the probe body 108 along the axis Z. This lateral movement with respect to the whole rectal retractor system 100 is also shown in FIG. 2 by arrow Z. Once the desired lateral position of the probe body 108 is set, a locking screw 186 (see FIG. 10) may be use to tighten the pair of apertures 182 of the support member 184 around the guide rods 180, thereby inhibiting lateral movement of the guide rods 180.

The stage 104 further includes a rotating knob 188 that extends through a main body 190 of the stage 104 to provide a fine height adjustment of the probe body 108. The main body 190 includes a substantially rectangular cut-out 192 through which the rotating knob 188 extends. A pair of vertical support rods 194 also extend through the cut-out 192 of the main body 190 and serve as a vertical guide for a support block 196. The support block 196 is coupled to the support member 184, such that as the rotating knob 188 is adjusted, the support block 196, and subsequently the support member 184, translate vertically. Therefore, the rotating knob 188 can provide a fine height adjustment of the probe body 108, as it is indirectly connected to the support member 184. In one embodiment, the main body 190 may further include numbered indicia (not shown) vertically disposed along a surface of the main body 190, for example, for accurate repositioning of the probe body 108 for subsequent treatments.

Figure 11:
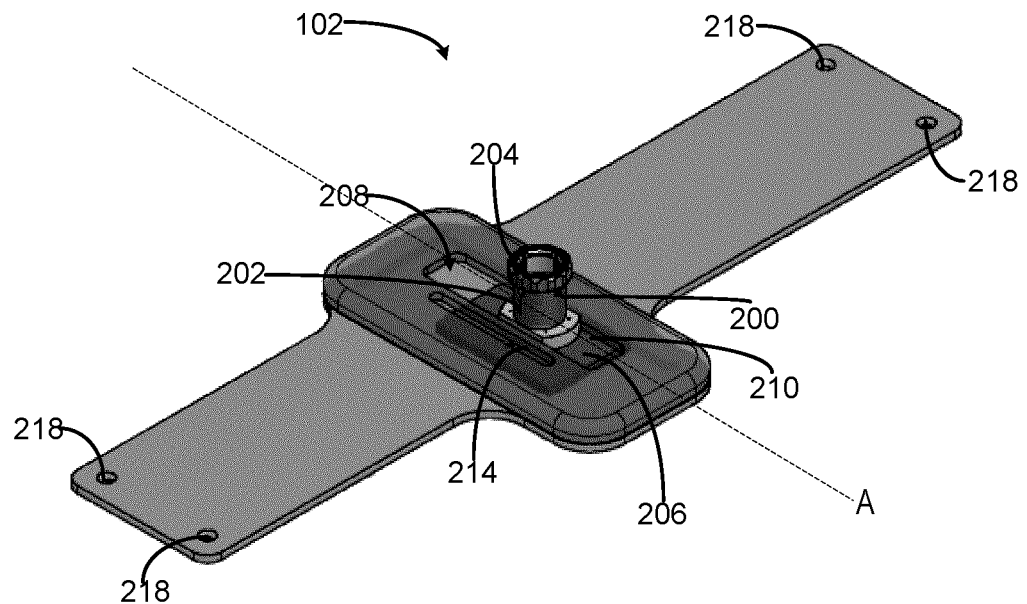
FIG. 11 is a perspective view of a base of the rectal retractor system for mounting on treatment couch.

Coupled to a lower end of the main body 190 of the stage 104 is a docking plug 198, as shown in FIG. 10, that is configured to be received by a docking socket 200 of the base 102 (see FIG. 11). The docking socket 200, similar to the docking socket 168 of the stage 104, may include external threads 202 for engaging internal threads (not shown) of a safety ring 204. Thus, once the docking plug 198 of the stage 104 is seated in the docking socket 200, the safety ring 204 may be rotated about the external threads 202 to secure the connection between the docking plug 198 and the docking socket 200.

Turning now to FIG. 11, the docking socket 200 may be coupled to and vertically extend from a base plate 206. In an alternative embodiment, the main body 190 of the stage 104 may be directly and/or integrally coupled to the base plate 206, thereby replacing the docking mechanism previously described. The base plate 206 is received by a cavity 208 of the base 102 so that the base plate 206 may translate along an axis A (also shown in FIG. 1 as arrow A). Translation along axis A allows the probe body 108 to be moved in any anterior-posterior direction. In addition, base 102 may include numbered indicia (not shown) disposed along a surface of the base 102, for example, for accurate repositioning of the probe body 108 along axis A for subsequent treatments.

In one example, an opening 210 into the cavity 208 may be dimensioned so that only translation of the base plate 206 occurs along the axis A to inhibit any rotational movement, for example, of the base plate 206. Once the anterior-posterior position of the base plate 206, and attached stage 104 and probe body 108, are in a desired position along the axis A, a locking spindle 212, which is coupled to the main body 190 of the stage (see FIG. 10), may be inserted into a slot 214 (see FIG. 11) of the base 102 and engage the base plate 206 to lock the stage 104 in place.

Figure 12:
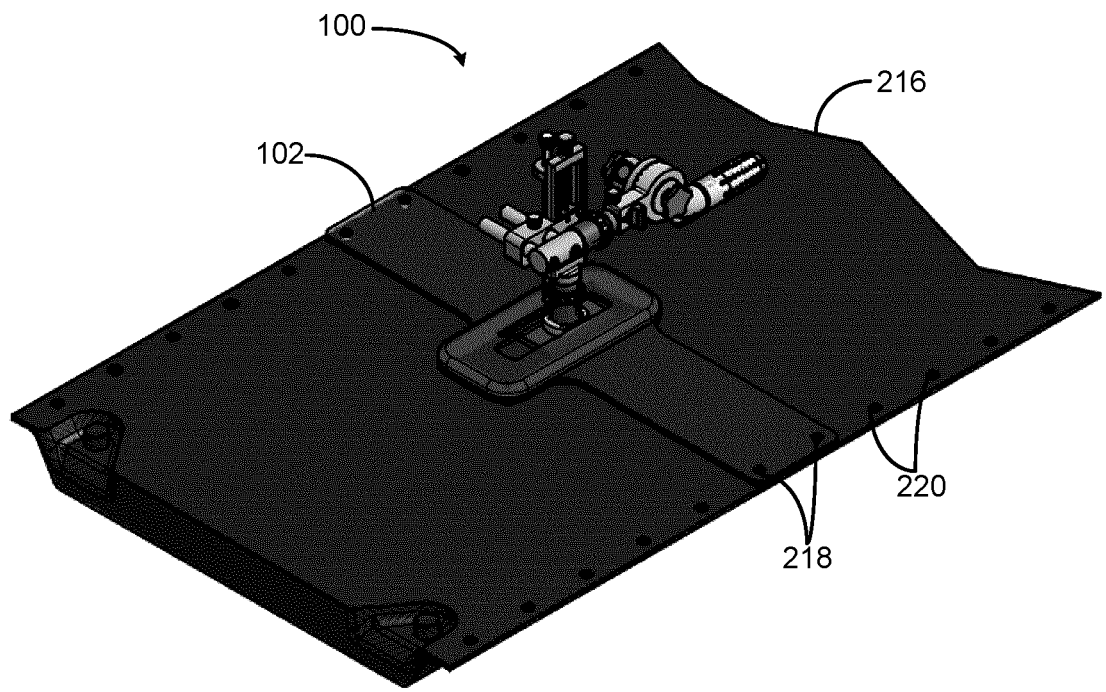
FIG. 12 is a perspective view of the rectal retractor system of FIG. 1 mounted on a treatment couch.

As shown in FIG. 12, the entire rectal retractor system 100 may be constructed to intimately connect with a treatment couch 216 such that the system 100 can only be oriented in one manner that will mitigate the risk of incorrect setup. In addition, by connecting the retractor system 100 to the treatment couch 216, motion of the patient and the patient's internal anatomy are limited. More specifically, the base 102 may include a plurality of apertures 218 configured to receive fasteners (not shown) that engage corresponding apertures 220 disposed on the treatment couch 216.

In one non-limiting example, during operation, a patient may be positioned in the lithotomy position and the probe body 108 may be inserted into the patient's rectum, for example. Prior to insertion of the probe body 108, various adjustments of the rectal retractor system 100 can be made to ensure reproducibility of the set-up. For example, the height of the probe body 108 may be adjusted by translating the square shaped member 126 in the opening 134 of the probe adjustment member 106 and locking it in place by tightening the locking handle 136. Additionally or alternatively, the probe body 108 may be rotated to a desired position and locked in place using the rotational locking knob 144 of the probe adjustment member 106, as shown in FIGS. 6 and 7. The probe body 108 may also be adjusted using any of the previously described adjustment mechanisms.

The probe body 108 is dimensioned to fixate the prostate and reduce target motion. In addition, the probe body 108 may also physically move the rectal wall out of the high does region. The distance between the prostate and rectum is increased by retraction of the rectum in posterior direction. This can reduce the dose to the rectum without compromising target coverage and also reduce movements of the prostate. The rectal retractor system 100 immobilizes the rectal wall and prevents changes in gas and faeces fillings. This reduces intrafractional motion of the rectum and ensures that the rectal wall does not move into the high does region of the beam. Therefore, interfractional motion does not influence the results as the retraction of the rectum is well reproduced between fractions.

EXAMPLE

A prior study was conducted, which treated 27 intermediate-risk prostate cancer patients with an endo-rectal balloon (ERB) achieved three-dimensional (3D) prostate displacements of 2.61±1.50 mm (CI95=±3.10 mm). In comparison, 3D prostate displacements observed in patients treated with the using the rectal retractor system 100 were significantly smaller at 1.83±0.75 mm (CI95=±1.47 mm), following a two-direction t-test (p=0.023, significance level $\alpha$=0.05). The translational displacements (95% confidence interval) were well-encompassed by the 3 mm applied PTV margin, as were the 3D displacements. None of the treated fractions had 3D displacements ≥3 mm. The fractional dose, and therefore treatment time, was also comparable for both studies (13.5 Gy per fraction versus 15 Gy per fraction).

The dosimetric impact of the observed prostate displacements on prostate coverage was also minimal for patients treated with the rectal retractor. Computation of treatment plans modelled using the prostate displacements observed during treatment showed the greatest change in CTV V100% with a drop of 2.67±1.47%; CTV V105% and V95% did not substantially change. None of the simulated plans had PTV coverage of <99% indicating that the dose detriment caused by prostate motion was still captured within the applied 3 mm PTV margin and the treatments are being delivered safely. In essence, this method offered robust and consistent intrafraction immobilization, highly comparable to that of the ERB, with limited impact on target coverage and dramatic improvements in doses to normal tissues (in comparison to patients treated with an ERB).

This study reported on the clinical use of the rectal retractor system 100 as part of a two-fraction SABR technique. The rectal retractor system 100 provided unparalleled immobilization of the prostate gland and enables end-to-end quality assurance of treatment delivery. The rectal retractor system 100 is minimally invasive and does not significantly impact target and OAR dosimetry, thereby allowing HDR brachytherapy-like distributions using SABR. The adoption of the rectal retractor system 100 has the potential of dramatically improving patient quality of life in addition to reducing the burden on departmental resources.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for monitoring doses from an ionizing radiation source to a treatment region of a patient, the system comprising:
   a probe body for insertion into a body cavity near the treatment region of the patient;
   a plurality of radiation detectors disposed along a proximal end of the probe body to measure at least one dose from the ionizing radiation source; and
   a slot disposed adjacent the plurality of radiation detectors, the slot configured to receive a dosimetry film that, upon exposure to the at least one dose from the ionizing radiation source, indicates a quantification of the at least one dose from the ionizing radiation source;
   wherein the probe body is dimensioned to separate a portion of the body cavity from the treatment region to reduce exposure of membranous tissue surrounding the body cavity to the at least one dose from the ionizing radiation source.

2. The system as recited in claim 1 wherein at least one of the probe body, the plurality of radiation detectors, and the dosimetry film are compatible with at least one of magnetic resonance imaging systems and computed tomography imaging system.

3. The system as recited in claim 1 wherein the body cavity is a rectum, and the probe body is dimensioned to immobilize the rectum so that the rectum does not move into a high dose treatment region.

4. The system as recited in claim 1 wherein the plurality of radiation detectors are optically stimulated luminescence (OSL) detectors.

5. The system as recited in claim 1 wherein the dosimetry film is at least one of a radiochromic film and a radiographic film.

6. The system as recited in claim 5 wherein the radiochromic film is a GafChromic film.

7. The system as recited in claim 6 wherein the GafChromic film is a GafChromic EBT3 film.

8. The system as recited in claim 1 further comprising:
a vertical stage including a docking socket for receiving a docking plunger coupled to the probe body; and
wherein the vertical stage includes at least one of a height adjustment, a lateral adjustment, a rotational adjustment and an anterior-posterior adjustment for the probe body.

9. The system as recited in claim 8 wherein the probe body and the vertical stage are configured for coupling to a treatment couch to limit incorrect set up of the probe body.

10. The system as recited in claim 1 further comprising:
a vertical stage coupled to the probe body, the vertical stage including a plurality of adjustments for the probe body; and
wherein the plurality of adjustments for the probe body correspond to a plurality of measurement guides to limit incorrect set up of the probe body.

11. The system as recited in claim 10 wherein the plurality of adjustments are adjusted using at least one of a thumb screw and a manual technique.

12. The system as recited in claim 1 further comprising:
a removable sheath including a plurality of perforations fluidly coupled to a passageway to passively remove gas from the body cavity.

13. The system as recited in claim 12 wherein the removable sheath includes a coupling in fluid communication with the passageway and configured to connect to a pump to actively remove gas from the body cavity.

14. The system as recited in claim 12 wherein the removable sheath provides active adherence of an inner wall of the body cavity to the probe body to increase immobilization of at least one of the body cavity and the treatment region.

15. The system as recited in claim 12 wherein the removable sheath includes a measurement guide disposed on an outer surface to provide reproducible set up of the probe body relative to the body cavity.

16. The system as recited in claim 1 wherein the probe body is constructed from a material that is at least one of capable of withstanding steam sterilization for reusability of the probe body and compatible with at least one of magnetic resonance imaging and x-ray imaging.

17. A method for providing end-to-end quality assurance, the steps of the method comprising:
providing a dosimetry film to the system recited in claim 1;
measuring a dose distribution by exposing the dosimetry film to radiation;
providing a planned dose distribution;
resampling the planned dose distribution to a plane of the dosimetry film; and
assessing quality assurance by comparing the resampled planned dose distribution with the measured dose distribution.

18. A device for immobilizing a body cavity relative to an anatomic region-of-interest, the device comprising:
a probe for insertion into the body cavity;
a removable sheath including a plurality of perforations formed in a surface thereof, the removable sheath configured to receive the probe; and
a coupling in fluid communication with the removable sheath, the coupling configured to be coupled to a pump to actively remove at least one of fluid and gas from the body cavity.

19. The device as recited in claim 18 wherein the body cavity is a rectum, and the probe is dimensioned to immobilize the rectum so that the rectum does not move into a high dose treatment region adjacent the anatomic region-of-interest.

20. The device as recited in claim 18 wherein probe includes a plurality of radiation detectors disposed along a proximal end of the probe to measure at least one dose from an ionizing radiation source.

21. The device as recited in claim 20 wherein the plurality of radiation detectors are optically stimulated luminescence (OSL) detectors.

22. The device as recited in claim 20 wherein the probe includes a slot disposed adjacent the plurality of radiation detectors, the slot configured to receive a dosimetry film that, upon exposure to the at least one dose from the ionizing radiation source, indicates a quantification of the at least one dose from the ionizing radiation source.

23. The device as recited in claim 22 wherein the dosimetry film is at least one of a radiochromic film and a radiographic film.

24. The device as recited in claim 23 wherein the radiochromic film is a GafChromic EBT3 film.

* * * * *